(12) United States Patent
Baba

(10) Patent No.: US 12,245,897 B2
(45) Date of Patent: Mar. 11, 2025

(54) FAILURE DETERMINATION APPARATUS OF ULTRASOUND DIAGNOSIS APPARATUS, FAILURE DETERMINATION METHOD, AND STORAGE MEDIUM

(71) Applicant: CANON KABUSHIKI KAISHA, Tokyo (JP)

(72) Inventor: Yoshitaka Baba, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 220 days.

(21) Appl. No.: 17/327,140

(22) Filed: May 21, 2021

(65) Prior Publication Data

US 2021/0369246 A1    Dec. 2, 2021

(30) Foreign Application Priority Data

Jun. 1, 2020    (JP) ................. 2020-095387

(51) Int. Cl.
    *A61B 8/00*    (2006.01)
    *G06N 20/00*   (2019.01)
(52) U.S. Cl.
    CPC ............... *A61B 8/54* (2013.01); *A61B 8/46* (2013.01); *G06N 20/00* (2019.01); *A61B 2560/0276* (2013.01)
(58) Field of Classification Search
    CPC .......... G06N 20/00; G06N 3/08; G06N 20/10; G06N 3/04; A61B 8/58; G01S 7/52; G01S 15/89
    See application file for complete search history.

(56) References Cited

U.S. PATENT DOCUMENTS

| 2020/0088862 | A1* | 3/2020 | Lundberg ................. G06N 3/04 |
| 2020/0322703 | A1* | 10/2020 | Bures ..................... G06N 20/00 |
| 2020/0380339 | A1* | 12/2020 | Branson ............... G06N 3/0499 |
| 2021/0121158 | A1* | 4/2021 | Tsymbalenko ......... A61B 6/505 |
| 2022/0296930 | A1* | 9/2022 | Chen .................... A61N 5/1075 |

FOREIGN PATENT DOCUMENTS

| JP | 2009172238 A | 8/2009 |
| JP | 2010172411 A | 8/2010 |
| WO | 2020056035 A1 | 3/2020 |
| WO | WO-2020232296 A1 * | 11/2020 |

* cited by examiner

*Primary Examiner* — Serkan Akar
*Assistant Examiner* — Aminah Asghar
(74) *Attorney, Agent, or Firm* — Canon U.S.A., Inc. IP Division

(57) ABSTRACT

A failure determination apparatus of an ultrasound diagnosis apparatus includes a determination unit configured to, using a trained model trained on data generated in a first ultrasound diagnosis apparatus in a failed state as supervised data, determine whether a second ultrasound diagnosis apparatus is in a failed state based on data generated in the second ultrasound diagnosis apparatus, and a notification unit configured to notify an operator of a result of determination by the determination unit.

14 Claims, 14 Drawing Sheets

FIG.7

| CASE | REFLECTED WAVE SIGNAL | SIGNAL PROCESSING DATA | ULTRASOUND IMAGE DATA | DETERMINATION |
|---|---|---|---|---|
| 1 | × | × | × | FAILED |
| 2 | × | × | ○ | FAILED |
| 3 | × | ○ | × | FAILED |
| 4 | × | ○ | ○ | POSSIBILITY OF FAILURE |
| 5 | ○ | ○ | ○ | NORMAL |
| 6 | ○ | ○ | × | NORMAL |
| 7 | ○ | × | ○ | NORMAL |
| 8 | ○ | × | × | POSSIBILITY OF FAILURE |
| 9 | — | × | × | FAILED |
| 10 | — | × | ○ | FAILED |
| 11 | — | ○ | × | NORMAL |
| 12 | — | ○ | ○ | NORMAL |

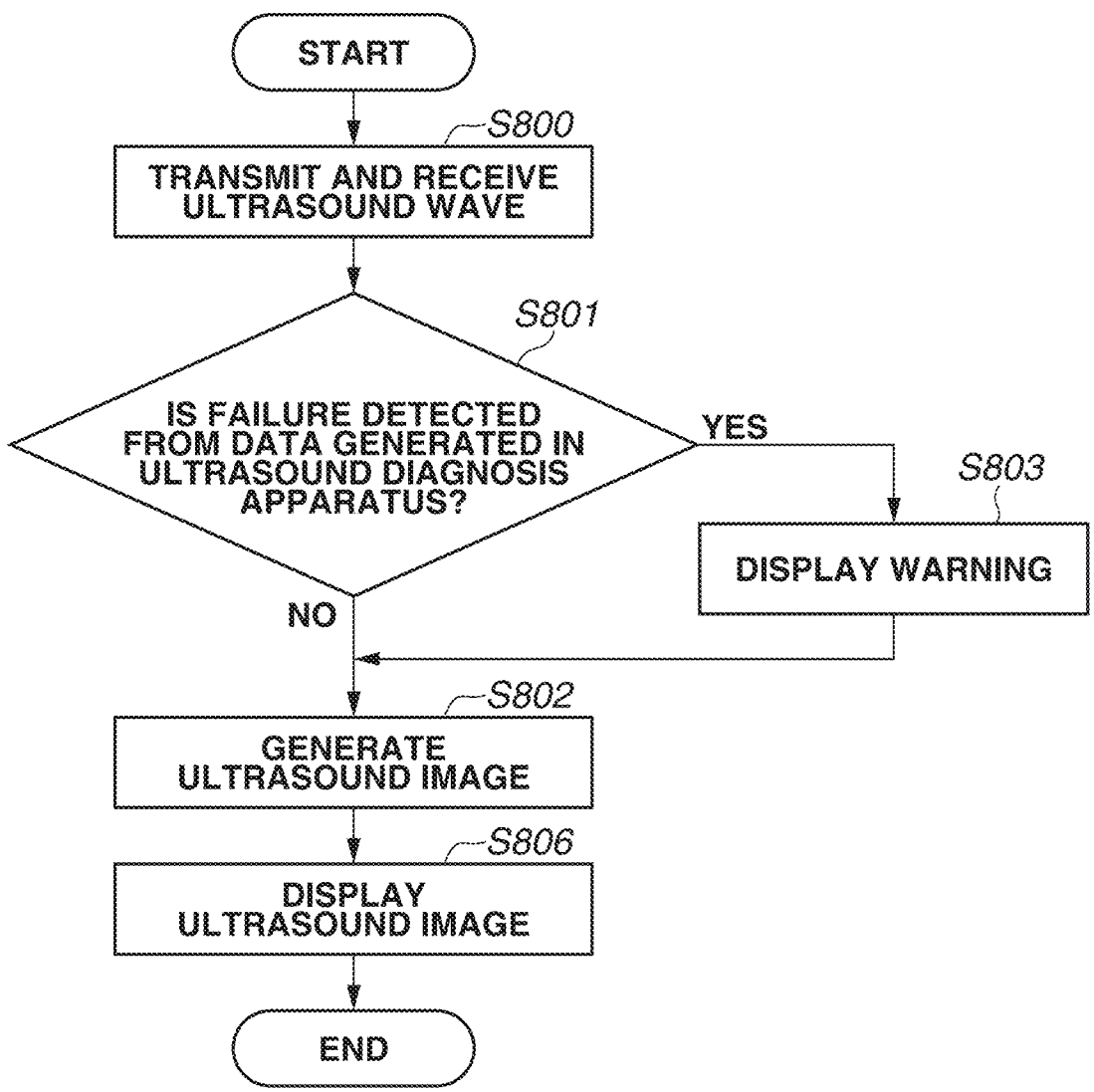

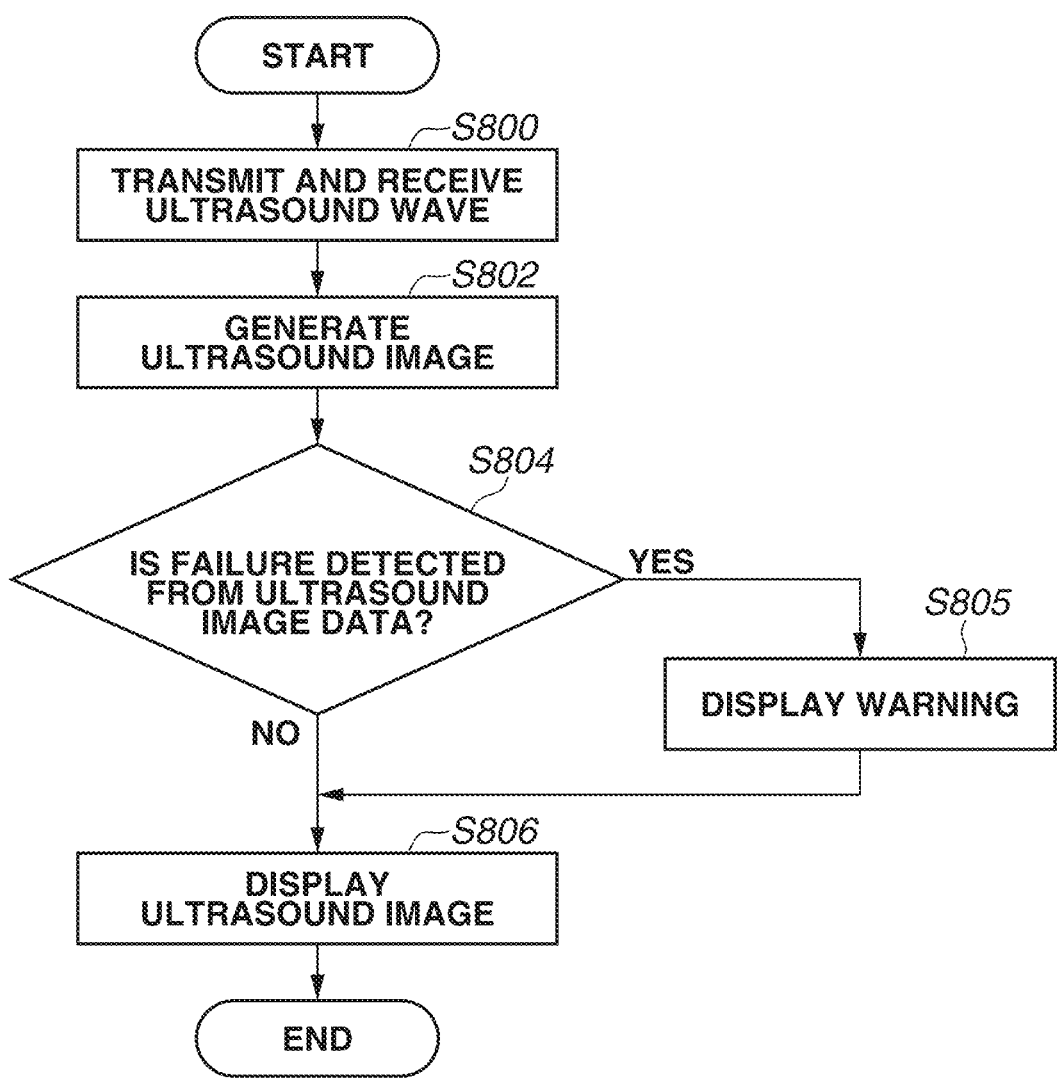

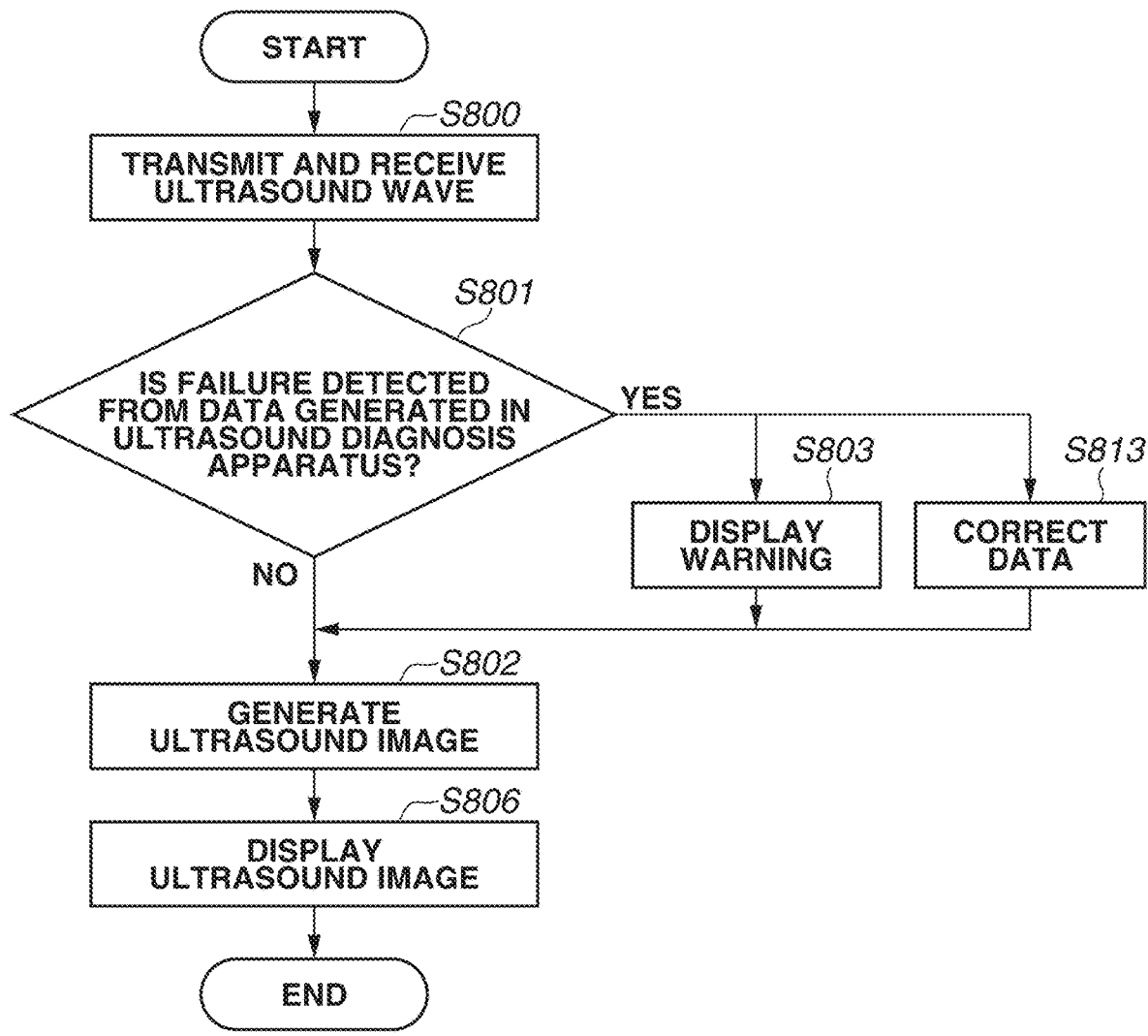

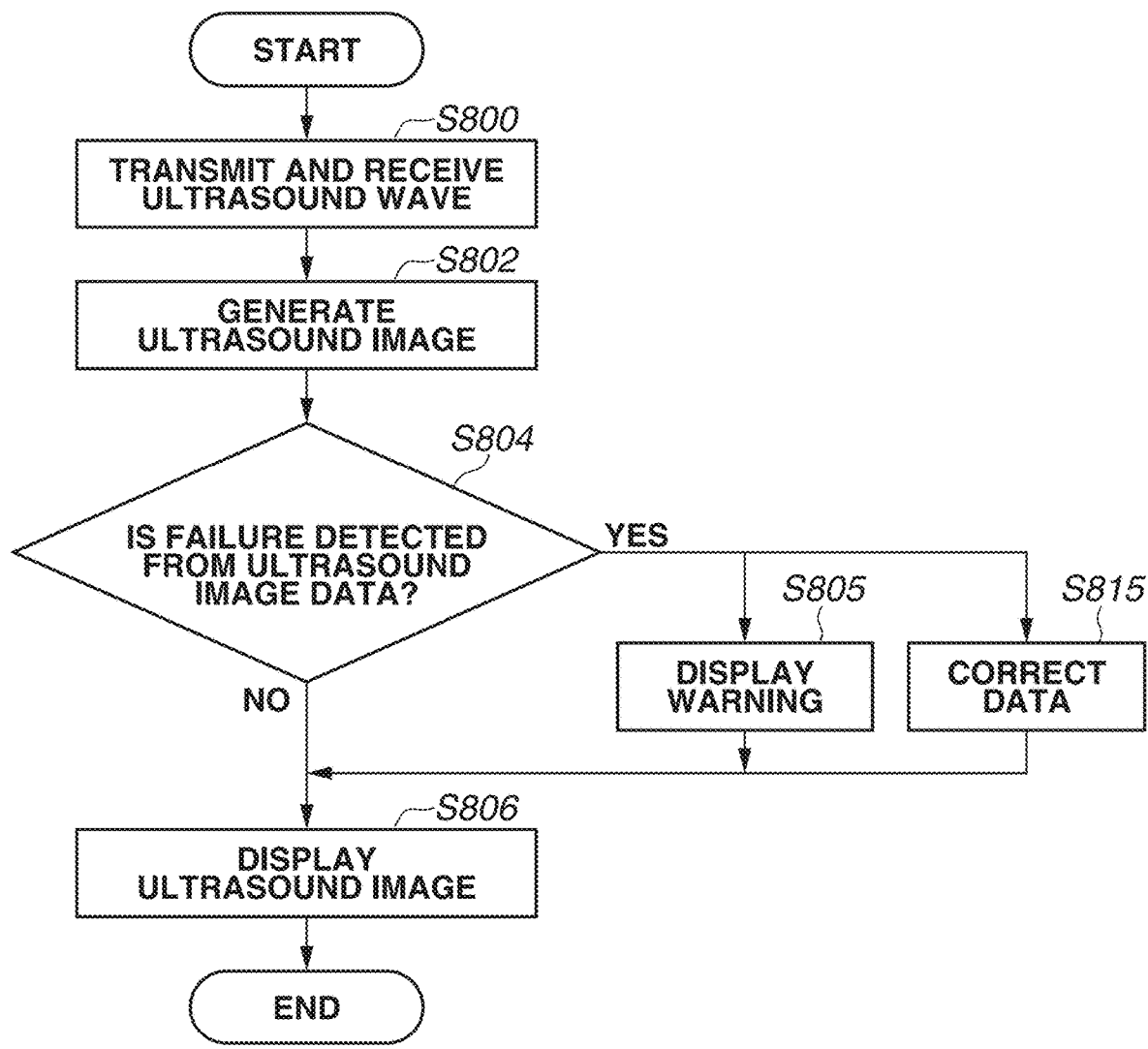

FAILURE DETERMINATION APPARATUS OF ULTRASOUND DIAGNOSIS APPARATUS, FAILURE DETERMINATION METHOD, AND STORAGE MEDIUM

BACKGROUND

Field of the Disclosure

The present invention relates to a failure determination apparatus capable of determining a failure in an ultrasound diagnosis apparatus, a failure determination method, and a storage medium.

Description of the Related Art

Some ultrasound diagnosis apparatus includes a self-diagnosis mode to determine a failure in the ultrasound diagnosis apparatus.

For example, Japanese Patent Application Laid-Open No. 2010-172411 discusses a technique for self-diagnosing the function of each of a plurality of transmission elements included in an ultrasound probe used in an ultrasound diagnosis apparatus and recovering the function of a transmission element that is impaired according to the self-diagnosis.

Japanese Patent Application Laid-Open No. 2010-172411, however, merely discusses a technique for self-diagnosing a particular element (a transmission element) in an ultrasound probe. Further, if a reception signal is not equivalent to a predetermined reference signal, it is determined that the particular element (the transmission element) is failed according to the technique by Japanese Patent Application Laid-Open No. 2010-172411.

SUMMARY OF THE INVENTION

The present disclosure is directed to providing a failure determination apparatus capable of making a failure determination with high accuracy of an ultrasound diagnosis apparatus.

A failure determination apparatus of an ultrasound diagnosis apparatus includes a determination unit configured to, using a trained model trained on data generated in a first ultrasound diagnosis apparatus in a failed state as supervised data, determine whether a second ultrasound diagnosis apparatus is in a failed state based on data generated in the second ultrasound diagnosis apparatus, and a notification unit configured to notify an operator of a result of determination by the determination unit.

Further features of the present invention will become apparent from the following description of exemplary embodiments with reference to the attached drawings.

BRIEF DESCRIPTION OF THE DRAWINGS

FIG. 7 is a diagram illustrating a determination form of the determination unit regarding the inference phase according to the first exemplary embodiment of the present invention.

FIG. 11 is a diagram illustrating an operation regarding the inference phase according to the first exemplary embodiment of the present invention.

FIG. 12 is a diagram illustrating an operation regarding the inference phase according to the first exemplary embodiment of the present invention.

FIG. 13 is a diagram illustrating an operation regarding the inference phase according to a second exemplary embodiment of the present invention.

FIG. 14 is a diagram illustrating an operation regarding the inference phase according to the second exemplary embodiment of the present invention.

DESCRIPTION OF THE EMBODIMENTS

With reference to the attached drawings, exemplary embodiments of the present invention will be described below.

Figure 1:
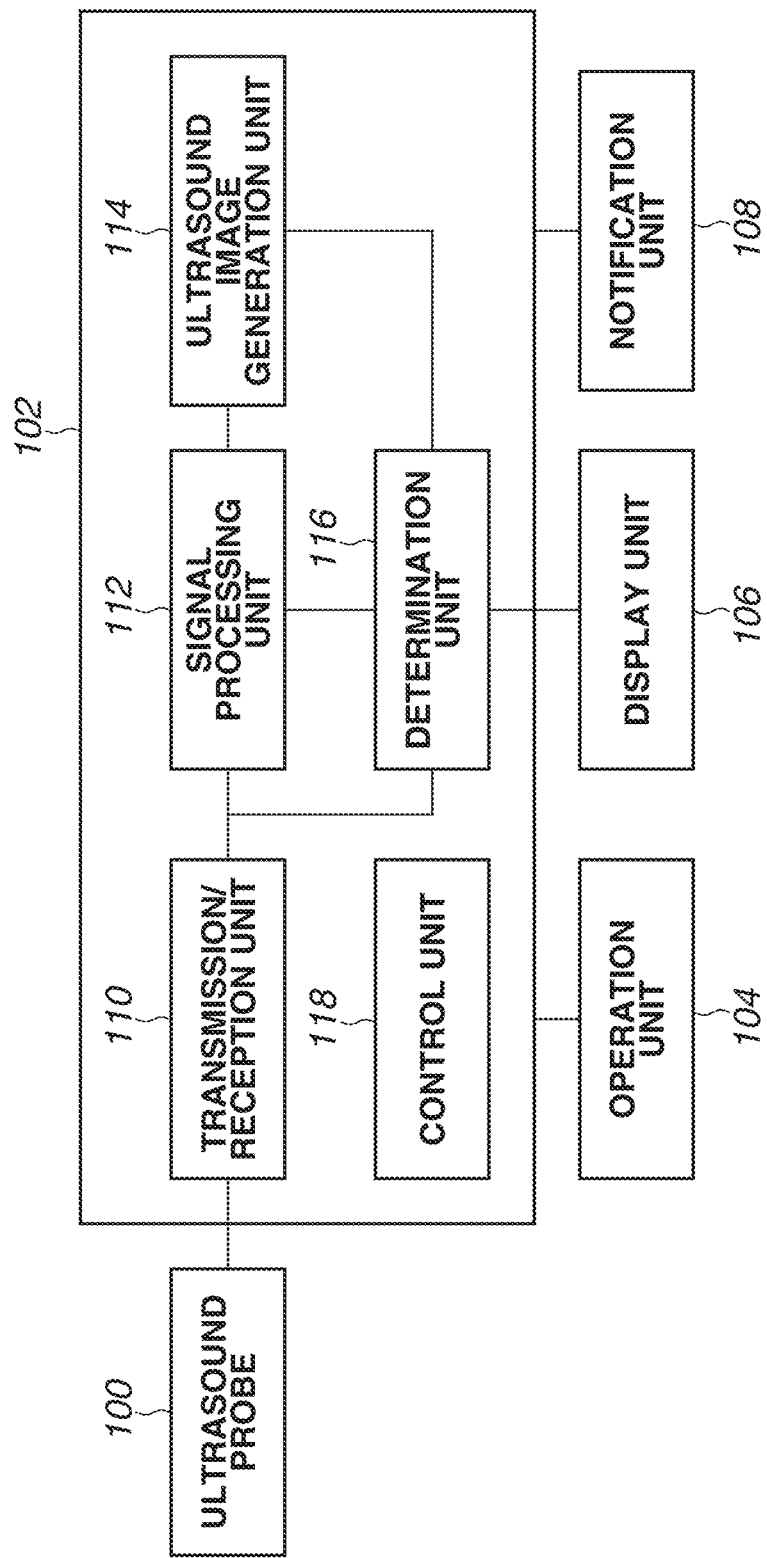
FIG. 1 is a diagram illustrating an overall configuration of an ultrasound diagnosis apparatus according to a first exemplary embodiment of the present invention.

A first exemplary embodiment is described below. FIG. 1 illustrates the configuration of an ultrasound diagnosis apparatus according to the present exemplary embodiment. The ultrasound diagnosis apparatus includes an ultrasound probe 100 that is brought into contact with a subject and transmits and receives an ultrasound wave, an apparatus main body 102 that generates an ultrasound image by processing an ultrasound signal received by the ultrasound probe 100 and makes various measurements, an operation unit 104 for operating the apparatus main body 102, and a display unit 106 that displays the ultrasound image and the measurement results.

The ultrasound probe 100 is connected to the apparatus main body 102. The ultrasound probe 100 includes a plurality of vibrators and can generate an ultrasound wave by driving the plurality of vibrators. The ultrasound probe 100 receives a reflected wave from the subject and converts the reflected wave into an electric signal. The converted electric signal is transmitted to the apparatus main body 102.

The ultrasound probe 100 includes an acoustic matching layer that is provided on the front surface side (the subject side) of the plurality of vibrators and matches the acoustic impedances of the plurality of vibrators and the subject, and a backing material that is provided on the back surface side of the plurality of vibrators and prevents the propagation of the ultrasound wave from the plurality of vibrators to the back surface side.

The ultrasound probe 100 is detachably connected to the apparatus main body 102. Examples of the type of the ultrasound probe 100 include a linear type, a sector type, a convex type, a radial type, and a three-dimensional scanning type. An operator can select the type of the ultrasound probe 100 depending on the purpose of imaging. The type of a sensor to be applied to the ultrasound probe 100 is not limited to a sensor using conventional bulk lead zirconate titanate (PZT), either. A capacitance probe of a type termed a capacitive micromachined ultrasonic transducer (CMUT) using a micromachining technique, or a probe of a type termed a piezoelectric micromachined ultrasonic transducer (PMUT) using a piezoelectric thin film technique in combination with the micromachining technique can be also used.

The apparatus main body 102 includes a transmission/reception unit 110, a signal processing unit 112, an ultrasound image generation unit 114, a determination unit 116 and a control unit 118. The transmission/reception unit 110 causes the ultrasound probe 100 to transmit and receive an ultrasound wave. The signal processing unit 112 performs various types of signal processing using an ultrasound signal based on a reflected wave signal received by the transmission/reception unit 110. The ultrasound image generation unit 114 generates ultrasound image data using signal processing data subjected to the signal processing by the signal processing unit 112. The determination unit 116 makes a failure determination using data such as the reflected wave signal received by the transmission/reception unit 110, the signal processing data subjected to the signal processing by the signal processing unit 112, and the ultrasound image data generated by the ultrasound image generation unit 114. The control unit 118 controls various components of the apparatus main body 102.

The transmission/reception unit 110 controls the transmission and reception of an ultrasound wave performed by the ultrasound probe 100. The transmission/reception unit 110 includes a transmission unit and a transmission delay circuit and supplies a driving signal to the ultrasound probe 100. The transmission unit repeatedly generates rate pulses at a predetermined pulse repetition frequency (PRF). The transmission delay circuit gives delay time for focusing an ultrasound wave generated by the ultrasound probe 100 and determining the transmission directionality of the ultrasound wave to the rate pulses generated by the transmission unit. The transmission delay circuit changes the delay time to be given to the rate pulses and thereby can control the transmission direction of an ultrasound wave to be transmitted from each vibrator.

The transmission/reception unit 110 also includes an amplifier, an analog-to-digital (A/D) conversion unit, a reception delay circuit, and an addition unit. The transmission/reception unit 110 performs various types of processing on a reflected wave signal received by the ultrasound probe 100, thereby generating an ultrasound signal. The amplifier amplifies the reflected wave signal for each channel and performs a gain correction process on the reflected wave signal. The A/D conversion unit performs A/D conversion on the reflected wave signal subjected to the gain correction. The reception delay circuit gives delay time for determining the reception directionality of the reflected wave signal to the digital data. The addition unit performs an addition process on the reflected wave signal to which the delay time is given by the reception delay circuit. The addition process of the addition unit emphasizes a reflection component from a direction according to the reception directionality of the reflected wave signal.

To two-dimensionally scan the subject, the transmission/reception unit 110 causes the ultrasound probe 100 to transmit a two-dimensional ultrasound wave. Then, the transmission/reception unit 110 generates a two-dimensional ultrasound signal from a two-dimensional reflected wave signal received by the ultrasound probe 100. To three-dimensionally scan the subject, the transmission/reception unit 110 causes the ultrasound probe 100 to transmit a three-dimensional ultrasound wave. Then, the transmission/reception unit 110 generates a three-dimensional ultrasound signal from a three-dimensional reflected wave signal received by the ultrasound probe 100.

The signal processing unit 112 performs various types of signal processing on the ultrasound signal output from the transmission/reception unit 110. Specifically, the signal processing unit 112 performs signal processing such as a wave detection process and logarithmic compression on the ultrasound signal. The signal processing unit 112 visualizes amplitude information regarding the ultrasound signal, thereby generating signal processing data (raster data). The signal processing unit 112 performs a band-pass filter process on the ultrasound signal output from the transmission/reception unit 110 and then detects the envelope of the output signal. Then, the signal processing unit 112 performs a compression process on data on the detected envelope by logarithmic transformation. The signal processing unit 112 outputs the signal processing data subjected to the signal processing to the ultrasound image generation unit 114.

The ultrasound image generation unit 114 generates ultrasound image data using the signal processing data subjected to the signal processing by the signal processing unit 112. The ultrasound image generation unit 114 includes a digital scan converter. Using the digital scan converter, the ultrasound image generation unit 114 converts the signal processing data into data represented by orthogonal coordinates. The ultrasound image generation unit 114 orthogonally transforms the signal processing data (the raster data) to a coordinate system (X, Y) of image data to be displayed. Then, the ultrasound image generation unit 114 generates ultrasound image data (B-mode image data) of which the signal intensity is represented by the brightness of luminance.

The determination unit 116 confirms data such as the reflected wave signal received by the transmission/reception unit 110, the various pieces of signal processing data (raster data), and the ultrasound image data and makes a failure determination in the ultrasound diagnosis apparatus.

Specifically, the determination unit 116 has a trained model trained on data generated in a first ultrasound diagnosis apparatus in a failed state as supervised data. Then, using the trained model, the determination unit 116 determines whether a second ultrasound diagnosis apparatus is in a failed state based on data generated in the second ultrasound diagnosis apparatus for use in diagnosing the subject. In the present exemplary embodiment, the first ultrasound diagnosis apparatus is an ultrasound diagnosis apparatus for generating a trained model using data acquired in advance (in the past). The second ultrasound diagnosis apparatus is a target ultrasound diagnosis apparatus used for determination of a failed state.

The operation unit 104 is composed of, for example, a mouse, a keyboard, a button, a panel switch, a touch command screen, a foot switch, a trackball, and a joystick. The operation unit 104 receives various instructions from the operator of the ultrasound diagnosis apparatus and transmits the received various instructions to the apparatus main body 102.

The display unit 106 displays a graphical user interface (GUI) for the operator to input various instructions using the operation unit 104 and displays an ultrasound image, a bloodstream image, and a measurement result generated in the apparatus main body 102. In a case where the determination unit 116 determines that the second ultrasound diagnosis apparatus is in a failed state, the display unit 106 indicates that the second ultrasound diagnosis apparatus is in the failed state. Although the display unit 106 is distinguished from a notification unit 108 in FIG. 1, the display unit 106 can also be regarded as the notification unit 108.

The transmission/reception unit 110, the signal processing unit 112, the ultrasound image generation unit 114, and the determination unit 116 in the apparatus main body 102 may be configured as hardware such as an integrated circuit or may be configured as a program modularized by software.

To make a failure determination, the ultrasound diagnosis apparatus according to the present exemplary embodiment uses a trained model trained to determine a failed state using data such as a received reflected wave signal, various pieces of signal processing data (raster data), and ultrasound image data. The trained model is, for example, a trained neural network, but may also be any model such as a deep learning model or a support-vector machine. The trained model may be stored in the determination unit 116 or may be connected to the ultrasound diagnosis apparatus via a network.

The first and second ultrasound diagnosis apparatuses are described below. The first ultrasound diagnosis apparatus is an ultrasound diagnosis apparatus in which a failure is actually caused or a failed state is simulated. The determination unit 116 learns data, such as a reflected wave signal, signal processing data, and ultrasound image data that are acquired from the first ultrasound diagnosis apparatus in a failed state, as supervised data, thereby generating a trained model. Using the trained model, the determination unit 116 determines a failed state of the second ultrasound diagnosis apparatus as a target of a failure determination and notifies the operator of the determination result.

The ultrasound image data to be input to the determination unit 116 (the trained model) may be two-dimensional image data or may be three-dimensional image data (volume data).

As described above, the trained model is trained to determine a failed state of the second ultrasound diagnosis apparatus. A trained model for determining a failed state based on two-dimensional image data may be used, or a trained model for determining a failed state based on three-dimensional image data may be used.

Figure 2:
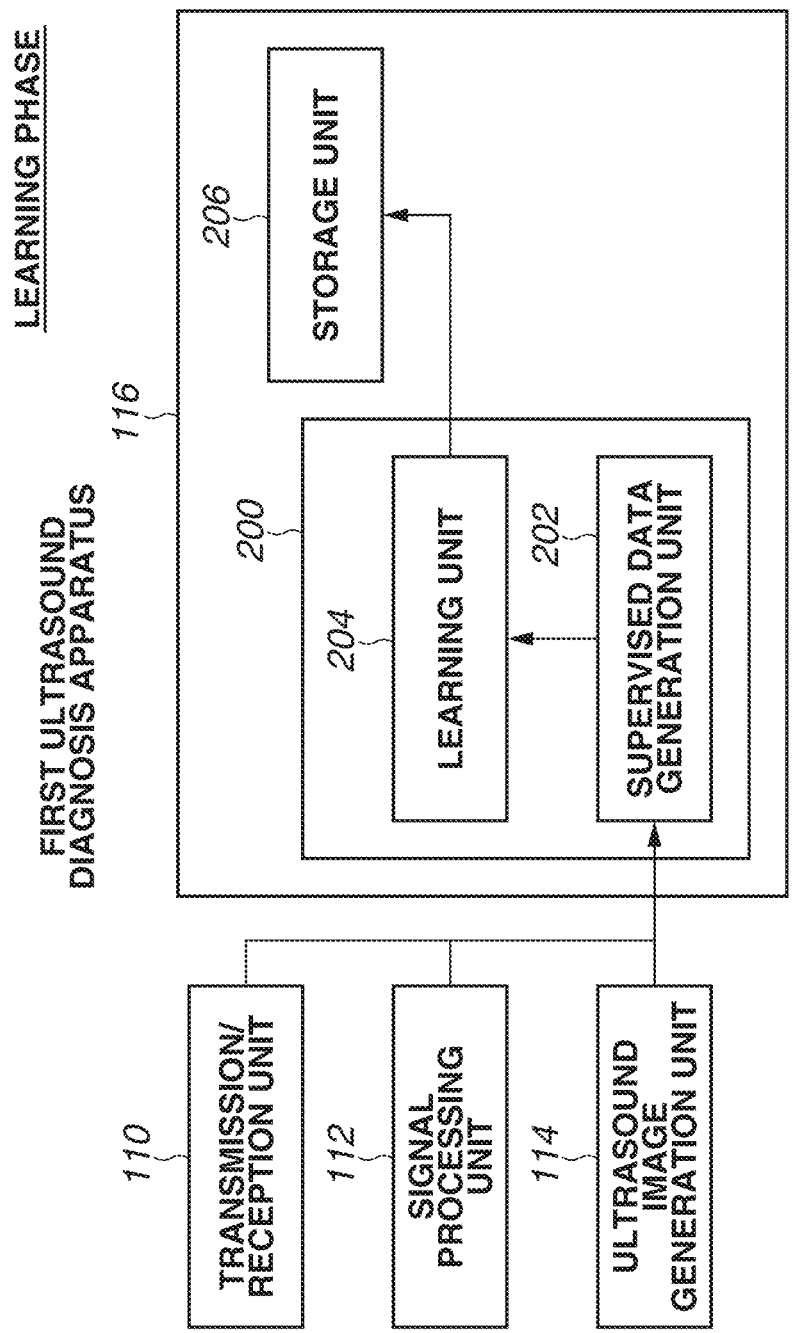
FIG. 2 is a diagram illustrating a determination unit regarding a learning phase according to the first exemplary embodiment of the present invention.
Figure 3:
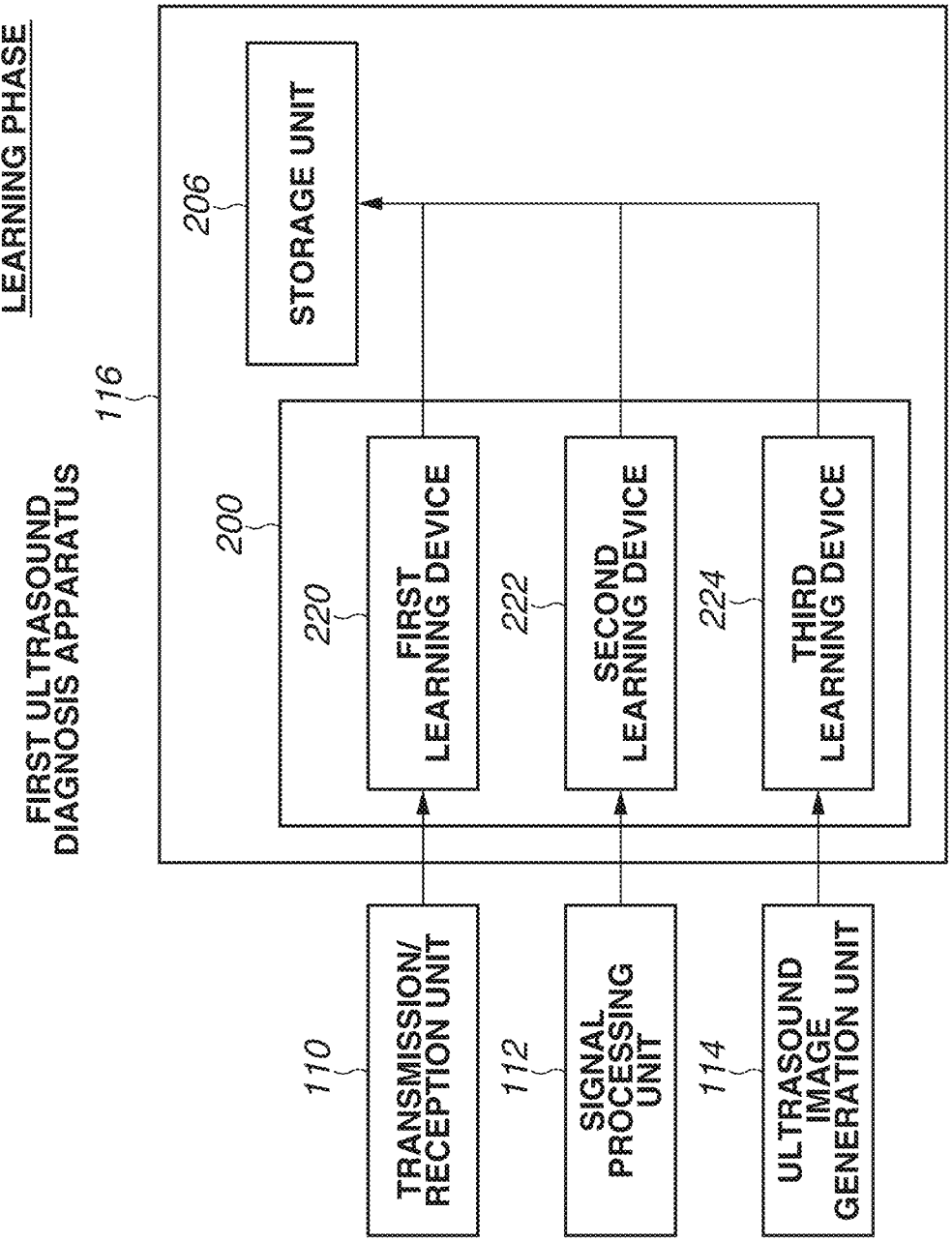
FIG. 3 is a diagram illustrating the determination unit regarding the learning phase according to the first exemplary embodiment of the present invention.
Figure 6:
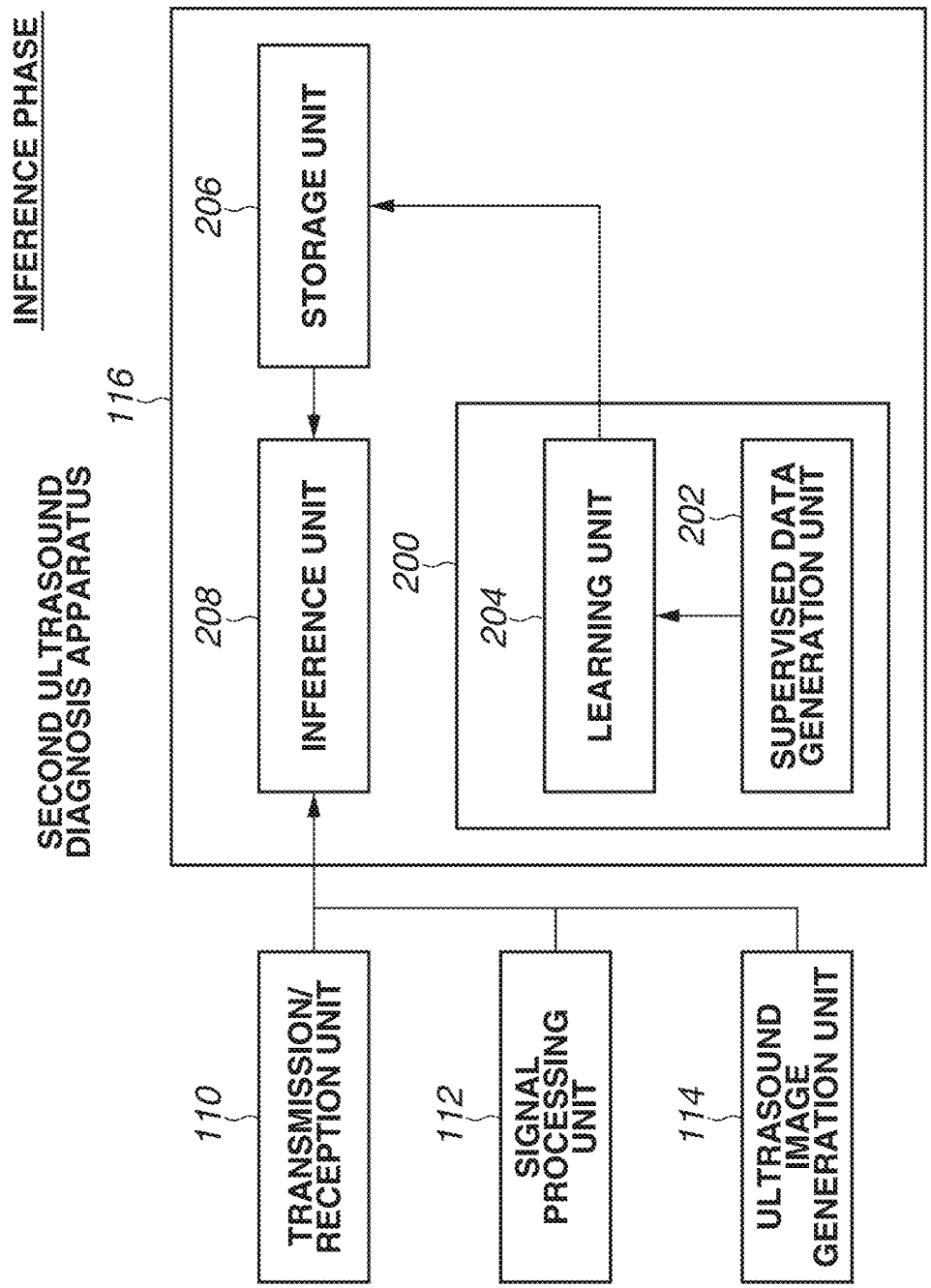
FIG. 6 is a diagram illustrating the determination unit regarding an inference phase according to the first exemplary embodiment of the present invention.

With reference to FIGS. 2, 3, and 6, the details of the determination unit 116 of the ultrasound diagnosis apparatus according to the present exemplary embodiment are described below. The general configurations of the determination unit 116 in FIGS. 2, 3, and 6 are similar to each other. The figures are differentiated to distinguish between operations regarding a learning phase and an inference phase. FIGS. 2 and 3 illustrate the operation of the determination unit 116 regarding a learning phase using the first ultrasound diagnosis apparatus. FIG. 6 illustrates the operation of the determination unit 116 regarding an inference phase using the second ultrasound diagnosis apparatus.

As illustrated in FIG. 2, the determination unit 116 includes a learning device 200 that learns data acquired from the first ultrasound diagnosis apparatus in a failed state as supervised data and thereby generates a trained model, and a storage unit 206 that stores the trained model generated by the learning device 200.

The learning device 200 includes a supervised data generation unit 202 and a learning unit 204. The supervised data generation unit 202 generates, based on data acquired from the first ultrasound diagnosis apparatus in a failed state, supervised data related to the failed state, and the learning unit 204 learns a failed state of the second ultrasound diagnosis apparatus using the supervised data generated by the supervised data generation unit 202.

The supervised data generation unit 202 generates supervised data using at least one of a reflected wave signal received by the transmission/reception unit 110, signal processing data subjected to signal processing by the signal processing unit 112, and ultrasound image data generated by the ultrasound image generation unit 114 in the first ultrasound diagnosis apparatus in a failed state.

The learning device 200 can actually cause a failure in the first ultrasound diagnosis apparatus and perform learning using data acquired from the first ultrasound diagnosis apparatus in the failed state. The learning device 200 can also set the first ultrasound diagnosis apparatus to the state where a failure is simulated, and perform learning using data acquired from the first ultrasound diagnosis apparatus in this state. Setting the first ultrasound diagnosis apparatus to the state where a failure is simulated means, for example, creating a disconnected state inside the first ultrasound diagnosis apparatus.

FIG. 3 illustrates a configuration including respective learning devices that learn a reflected wave signal received by the transmission/reception unit 110, signal processing data subjected to signal processing by the signal processing unit 112, and ultrasound image data generated by the ultrasound image generation unit 114. The learning devices generate trained models according to the types of data generated in the first ultrasound diagnosis apparatus.

Specifically, the learning device 200 includes a first learning device 220, a second learning device 222 and a third learning device 224. The first learning device 220 performs learning using a reflected wave signal received by the transmission/reception unit 110 in the first ultrasound diagnosis apparatus in a failed state, thereby generating a first trained model. The second learning device 222 performs learning using signal processing data subjected to signal processing by the signal processing unit 112 in the first ultrasound diagnosis apparatus in the failed state, thereby generating a second trained model. The third learning device 224 performs learning using ultrasound image data generated by the ultrasound image generation unit 114 in the first ultrasound diagnosis apparatus in the failed state, thereby generating a third trained model. The learning device 200 may only need to generate a plurality of trained models, and the plurality of trained models are not limited to the three trained models (the first, second, and third trained models).

Based on the reflected wave signal received by the first ultrasound diagnosis apparatus, a change in the noise level and a change in the noise band characteristics can be obtained. At this time, an ultrasound wave can also be transmitted and received without bringing the ultrasound probe 100 into contact with the subject. Then, based on the amplitude and the band characteristics of the reflected wave signal, the crosstalk level, and the state of multiple reflection, it can be determined in which of elements of the channels of the ultrasound probe 100 a failed circuit or wiring has occurred. Thus, the first trained model can be generated using this reflected wave signal as supervised data.

Based on the signal processing data subjected to the signal processing by the first ultrasound diagnosis apparatus, if an element group to be selected in transmission and reception is changed, for example, pieces of data on different scan lines are compared with each other. Then, as a result of comparing the pieces of data on the scan lines, it can be determined which channel a failed circuit belongs to. Thus, the second trained model can be generated using this signal processing data as supervised data.

Based on the ultrasound image data generated in the first ultrasound diagnosis apparatus, similarly, if an element group to be selected in transmission and reception is changed, for example, pieces of image data on different scan lines are compared with each other. Then, as a result of comparing the pieces of image data on the scan lines, it can be determined which channel a failed circuit belongs to. Thus, the third trained model can be generated using this ultrasound image data as supervised data.

Figure 4:
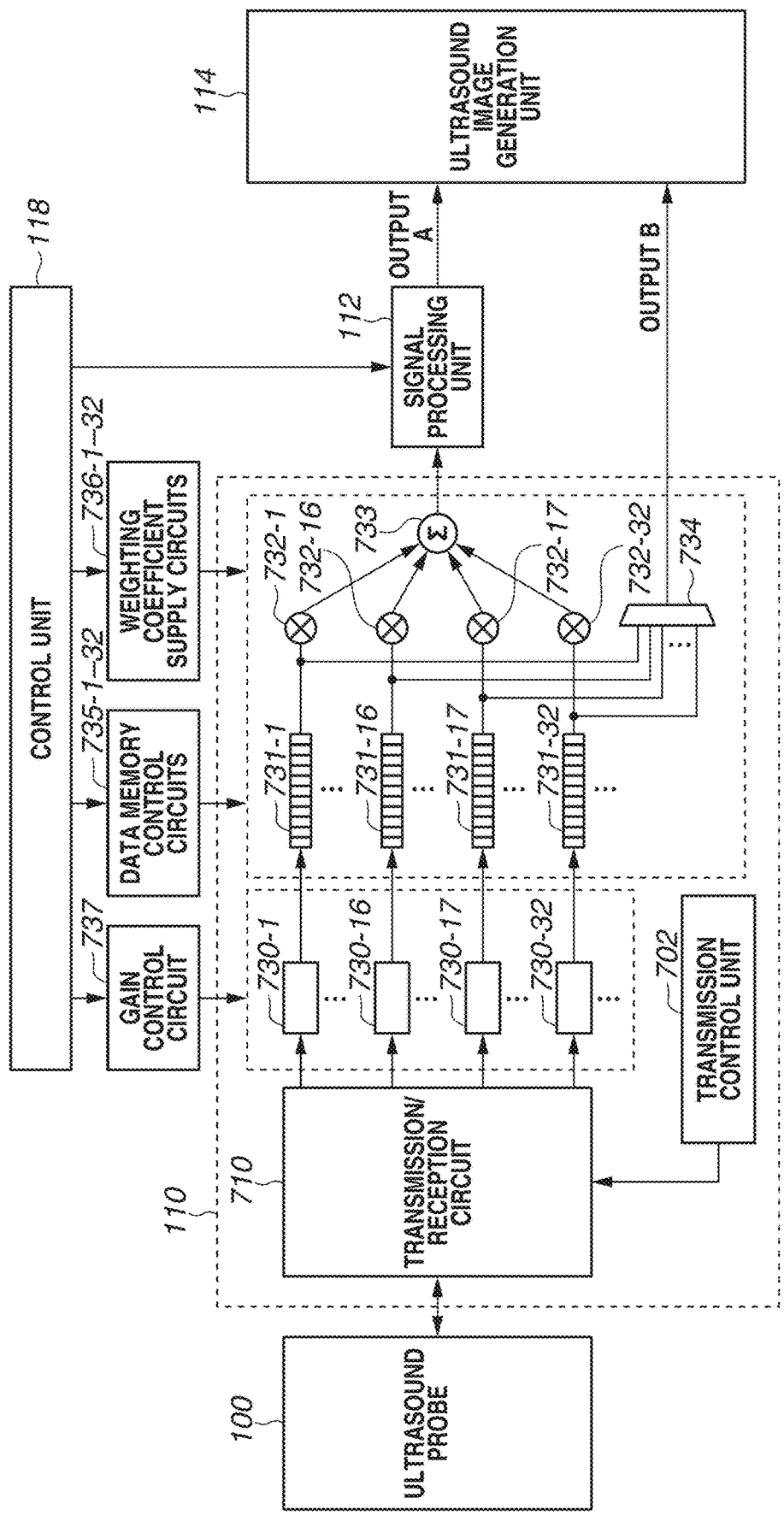
FIG. 4 is a diagram illustrating an internal configuration of the ultrasound diagnosis apparatus according to the first exemplary embodiment of the present invention.

FIG. 4 is a diagram illustrating the internal configuration of the ultrasound diagnosis apparatus according to the present exemplary embodiment. FIG. 4 is a diagram illustrating the configurations of the transmission/reception unit 110, the signal processing unit 112, the ultrasound image generation unit 114, and the periphery of these units according to the present exemplary embodiment. FIG. 4 illustrates a case where the transmission/reception unit 110 includes 32 channels. The number of channels of the transmission/reception unit 110, however, does not necessarily need to be limited to 32 channels, and can be appropriately determined according to the specification of the ultrasound diagnosis apparatus.

The transmission/reception unit 110 in FIG. 4 includes a transmission/reception circuit 710 that transmits and receives an ultrasound wave, A/D conversion units 730-1 to 730-32 that convert a reflected wave signal received by the ultrasound probe 100 from an analog signal to a digital signal, data memories 731-1 to 731-32 that store data on the digital signal, and a multiplexer 734 that selects any of data output ports of the data memories 731-1 to 731-32 and connects the selected data output port to the ultrasound image generation unit 114. The transmission/reception unit 110 also includes apodization multipliers 732-1 to 732-32 and an addition circuit 733. The transmission/reception unit 110 may also include data memory control circuits 735-1 to 735-32, weighting coefficient supply circuits 736-1 to 736-32, and a gain control circuit 737.

The transmission waveform of an ultrasound wave generated by a transmission control unit 702 is transmitted from the ultrasound probe 100 via the transmission/reception circuit 710.

An ultrasound signal acquired by the ultrasound probe 100 and converted into an analog electric signal passes through the transmission/reception circuit 710 and is converted into a digital signal by the A/D conversion units 730-1 to 730-32. At this time, the A/D conversion units 730-1 to 730-32 sample the ultrasound signal using a sampling clock supplied from a clock source (not illustrated) and convert the analog electric signal into the digital signal. The clock source (not illustrated) supplies an appropriate sampling clock to the A/D conversion units 730-1 to 730-32 according to the frequency range of the ultrasound signal to be acquired.

Depending on the performances of the A/D conversion units 730-1 to 730-32, the A/D conversion units 730-1 to 730-32 each output a digital signal having a bit width of about 12 bits to 16 bits. The digital signals output from the A/D conversion units 730-1 to 730-32 are loaded into the corresponding data memories 731-1 to 731-32 based on the control of the data memory control circuits 735-1 to 735-32. The data memories 731-1 to 731-32 have capacity capable of storing digital signals corresponding to the maximum measurement depth of the subject.

Further, the gain control circuit 737 performs gain control, such as time gain compensation (TGC) control, on the A/D conversion units 730-1 to 730-32. For example, to acquire ultrasound image data having uniform contrast regardless of the measurement depth, an amplification gain is increased or decreased according to the time from the transmission of the ultrasound wave to the reception of the ultrasound wave. By performing the TGC control, ultrasound image data having uniform contrast can be acquired.

The control unit 118 performs control for writing digital signals output from the A/D conversion units 730-1 to 730-32 to the data memories 731-1 to 731-32. Additionally, the control unit 118 can also control the multiplexer 734 to select any of the data memories 731-1 to 731-32, read a digital signal, and transfer the digital signal to the ultrasound image generation unit 114. When this control is performed, the ultrasound image generation unit 114 generates ultrasound image data not via the apodization multipliers 732-1 to 732-32, the addition circuit 733 or the signal processing unit 112. In many cases, the control unit 118 sequentially selects all the data memories 731-1 to 731-32, reads a digital signal, and transfers the digital signal to the ultrasound image generation unit 114.

The ultrasound image generation unit 114 generates ultrasound image data. An image can be reconfigured by applying not only a phasing addition process but also any algorithm as an algorithm for generating the ultrasound image data.

Typically, when an ultrasound image is generated, phasing addition is performed. However, there is a case where an image is reconfigured by applying an algorithm other than the phasing addition. Examples of another image reconfiguration method include a back projection method with a time domain or a Fourier domain, which is normally used in the tomographic technique. As described above, an image may be reconfigured by applying any algorithm other than the phasing addition process.

The output voltage or the output waveform of the transmission control unit 702 may be converted into data, and data on a failed state in this data may be used as supervised data. Alternatively, paying attention to waveform data on a waveform output from the transmission control unit 702 and reflected by the ultrasound probe 100, a trained model may be generated using data on a failed state in the waveform data on the reflected waveform as supervised data.

Further it can be determined which channel circuit of the transmission/reception circuit 710 has failed. Specifically, items to be confirmed are the peak level of waveform data, the rise and fall characteristics of the waveform, the band characteristics of the waveform, and the crosstalk. As a result of confirming these items, the causes of the failure of a transmission circuit power supply, the failure of a driver circuit of a transmission circuit, and the defect of a transmission circuit board can be isolated. Items to be subject to failure detection, however, are not necessarily limited to these. The items are not limited to particular items so long as the items can cause the deterioration of the transmission characteristics of the ultrasound diagnosis apparatus.

A technique for transmitting an ultrasound wave for generating data to which a failure determination is applied is not limited to a particular method, either. For example, in addition to a focused transmission beam, a transmission waveform such as a planar wave or a diffuse wave can be used. The technique is not limited to a particular transmission technique so long as a transmission waveform effective in an ultrasound image diagnosis or a failure determination is used.

As described above, the ultrasound diagnosis apparatus according to the present exemplary embodiment can not only determine that a failure occurs, but also determine which portion is failed.

To determine a failed state in detail, data calculated as a result of performing addition, subtraction, multiplication, and division processes on data or processing data by performing any combination of these processes may be used as supervised data. This corresponds to a case where Fourier transform or a differentiation process such as edge detection is performed on a transmission waveform, a reception waveform, or image data, and the resulting data is used as supervised data. Alternatively, the result of making an inference on data generated in the ultrasound diagnosis apparatus by using artificial intelligence can also be used as supervised data.

For example, the learning device 200 may perform learning using digital signals stored in the data memories 731-1 to 731-32 and output from the multiplexer 734. Alternatively, the learning device 200 may perform learning using data output from the addition circuit 733 and the signal processing unit 112. Data to be used as supervised data by the learning device 200 may be data in any portion of a processing flow performed to generate an ultrasound image in the ultrasound diagnosis apparatus. The type of the data and the combination of the data are not limited to a particular type or a particular combination.

As described above, the learning unit 204 can learn the characteristics of a failed state of the ultrasound diagnosis apparatus using any data processed by the ultrasound diagnosis apparatus.

Examples of data generated in the ultrasound diagnosis apparatus are illustrated below. For example, reflected wave signal data corresponds to digital signals output from the A/D conversion units 730-1 to 730-32 or digital signals stored in the data memories 731-1 to 731-32 and output from the multiplexer 734. Signal processing data corresponds to data output from the signal processing unit 112. Ultrasound image data corresponds to ultrasound image data generated by the ultrasound image generation unit 114. However, in a case where the ultrasound image generation unit 114 includes a plurality of signal processing blocks or a plurality of image processing blocks, the output of each signal processing block or each image processing block also corresponds to the ultrasound image data. Any portion of the data flow of the ultrasound diagnosis apparatus may be used for a failure determination so long as the portion is useful in the failure determination. The portion is not limited to a particular portion.

Figure 5:
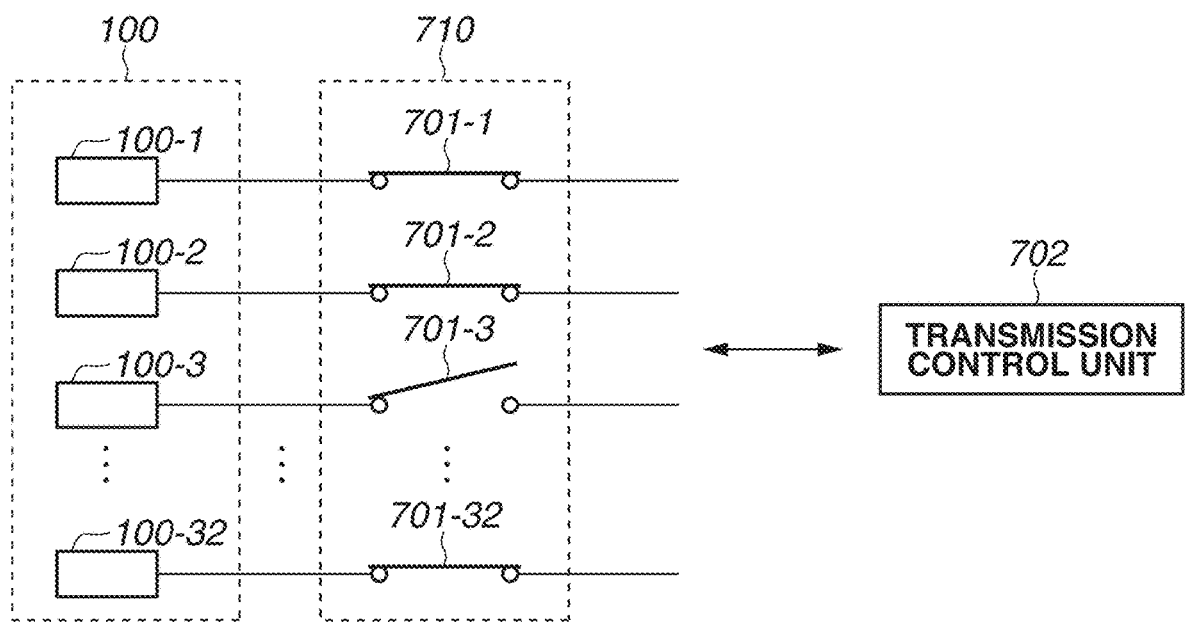
FIG. 5 is a diagram illustrating an example of a first ultrasound diagnosis apparatus in a failed state according to the first exemplary embodiment of the present invention.

FIG. 5 illustrates an example of the first ultrasound diagnosis apparatus in a failed state. In a normal state, the transmission/reception circuit 710 connect all vibrators 100-1 to 100-32 in the ultrasound probe 100 to the transmission control unit 702. A part 701-3 of the transmission/reception circuit 710 is brought into an open state, so that a failed state (a disconnected state in this case) can also be created. Similarly, the operation setting of another circuit of the first ultrasound diagnosis apparatus can be made different from that in the normal state, so that a failed state can be created in a simulated manner Then, the failed state of the first ultrasound diagnosis apparatus can be learned.

An external apparatus can also generate by simulation a reflected wave signal, signal processing data, and ultrasound image data that are generated from the first ultrasound diagnosis apparatus in a failed state, and use the generated data for learning. The data to be generated by simulation may be data obtained by simulating a failed state in any combination of data on a two-dimensional or three-dimensional still image or a two-dimensional or three-dimensional moving image captured in the state where the ultrasound diagnosis apparatus is not actually failed. Alternatively, the data to be generated by simulation may be data obtained by creating a failed state in data acquired by performing simulation using one or more simulation models different from each other in the size, the location, or the physical property of a wire phantom or a cyst phantom.

For example, the learning unit 204 uses a neural network, which includes a plurality of layers. The plurality of layers includes a plurality of intermediate layers between an input layer and an output layer. Although not illustrated, the plurality of intermediate layers includes a convolution layer, a pooling layer, an upsampling layer, and a combining layer. The convolution layer is a layer that performs a convolution process on an input value group. The convolution layer performs a convolution process on an input ultrasound image (a region of interest) and extracts the feature of the ultrasound image (the region of interest).

The pooling layer is a layer that performs the process of thinning out an input value group or combining input value groups to reduce the number of output value groups to be smaller than the number of input value groups. The upsampling layer is a layer that performs the process of duplicating an input value group or adding a value interpolated from an input value group to increase the number of output value groups to be greater than the number of input value groups. The combining layer is a layer that performs the process of inputting value groups such as output value groups on a certain layer or pixel value groups included in an ultrasound image (a region of interest) from a plurality of sources and joining or adding these value groups to combine the value groups. The number of intermediate layers can be changed as needed according to the learning content.

As described above, the learning device 200 (the learning unit 204) learns data on a failed state of the ultrasound diagnosis apparatus as supervised data in an associated manner using a neural network, thereby generating a trained model.

With reference to FIG. 6, the operation of the determination unit 116 regarding the inference phase is described below. In a learning device 200, a trained model related to target data to be used in a failure determination in the second ultrasound diagnosis apparatus is generated. A storage unit 206 is connected to the learning device 200. The storage unit 206 stores a trained model trained to determine a failed state. Specifically, the storage unit 206 stores a trained model trained to determine a failed state based on data acquired from the second ultrasound diagnosis apparatus.

For example, the storage unit 206 stores a first trained model generated by a first learning device 220, a second trained model generated by a second learning device 222, and a third trained model generated by a third learning device 224.

Then, a reflected wave signal received by a transmission/reception unit 110 in the second ultrasound diagnosis apparatus is output to an inference unit 208. The inference unit 208 reads from the storage unit 206 the first trained model trained to determine a failed state. Then, using the first trained model, the inference unit 208 determines a failed state based on the reflected wave signal received by the transmission/reception unit 110. Signal processing data subjected to signal processing by a signal processing unit 112 in the second ultrasound diagnosis apparatus is output to the inference unit 208. The inference unit 208 reads from the storage unit 206 the second trained model trained to determine a failed state. Then, using the second trained model, the inference unit 208 determines a failed state based on the signal processing data subjected to the signal processing by the signal processing unit 112. Further, ultrasound image data generated by an ultrasound image generation unit 114 in the second ultrasound diagnosis apparatus is output to the inference unit 208. The inference unit 208 reads from the storage unit 206 the third trained model trained to determine a failed state. Then, using the third trained model, the inference unit 208 determines a failed state based on the ultrasound image data output from the ultrasound image generation unit 114.

A form has been illustrated in which the transmission/reception unit 110, the signal processing unit 112, and the ultrasound image generation unit 114 are linked to the inference unit 208. The present exemplary embodiment, however, is not necessarily limited to this form. Any data and any combination of data used in the ultrasound diagnosis apparatus can be linked to the inference unit 208 and used to determine a failed state.

For example, any of reflected wave signal data, signal processing data, and ultrasound image data acquired from the ultrasound diagnosis apparatus and any combination of these pieces of data can be linked to the inference unit 208 and used for a failure determination. The data to be linked to the inference unit 208 for the failure determination is not limited to a particular type of data so long as the data is useful in the failure determination.

With reference to FIG. 7, the determination form of the determination unit 116 regarding the inference phase is described below. Cases 1 to 12 illustrated in FIG. 7 are examples of determination using a reflected wave signal, signal processing data, and ultrasound image data. The determination unit 116 sets a degree of priority according to the type of data generated in the second ultrasound diagnosis apparatus, and determines whether the second ultrasound diagnosis apparatus is in a failed state according to the degree of priority. The degree of priority is set, for example, with respect to each of the reflected wave signal, the signal processing data, and the ultrasound image data. The degree of priority may be set also for each of another signal and another piece of data generated in the second ultrasound diagnosis apparatus. The operator can set the degree of priority using the operation unit 104. The degree of priority is weighted according to the data processing content, and for example, weights can be set for the reflected wave signal, the signal processing data, and the ultrasound image data in this order.

In FIG. 7, a sign "×" indicates a form in which it is determined based on the reflected wave signal that the second ultrasound diagnosis apparatus is in a failed state, a form in which it is determined based on the signal processing data that the second ultrasound diagnosis apparatus is in a failed state, and a form in which it is determined based on the ultrasound image data that the second ultrasound diagnosis apparatus is in a failed state. A sign "○" indicates a form in which it is determined based on the reflected wave signal that the second ultrasound diagnosis apparatus is in a normal state, a form in which it is determined based on the signal processing data that the second ultrasound diagnosis apparatus is in the normal state, and a form in which it is determined based on the ultrasound image data that the second ultrasound diagnosis apparatus is in the normal state.

Cases 1 to 8 are forms in which the state of the second ultrasound diagnosis apparatus is determined using three pieces of data (the reflected wave signal, the signal processing data, and the ultrasound image data). Although the three pieces of data are described in the present exemplary embodiment, the data to be used is not limited to these pieces of data, and another piece of data can also be applied.

In case 1, the reflected wave signal, the signal processing data, and the ultrasound image data are all indicated by the sign "×". The determination unit 116 determines that the second ultrasound diagnosis apparatus is in a failed state.

In case 2, the reflected wave signal and the signal processing data are indicated by the sign "×", and the ultrasound image data is indicated by the sign "○". In a case where the determination of the reflected wave signal and the signal processing data and the determination of the ultrasound image data are different from each other, the determination in the upstream processing in the ultrasound diagnosis apparatus takes priority. In this case, the priority relationship is as follows: the determination of the reflected wave signal >the determination of the signal processing data >the determination of the ultrasound image data. Since the reflected wave signal and the signal processing data are indicated by the sign "×", the determination unit 116 determines that the second ultrasound diagnosis apparatus is in a failed state.

In case 3, the reflected wave signal and the ultrasound image data are indicated by the sign "×", and the signal processing data is indicated by the sign "○". Since the reflected wave signal is indicated by the sign "×", the determination unit 116 determines that the second ultrasound diagnosis apparatus is in a failed state based on the above-described priority relationship.

In case 4, the reflected wave signal is indicated by the sign "×", and the ultrasound image data and the signal processing data are indicated by the sign "○". Although the reflected wave signal is indicated by the sign "×", the other two pieces of data are indicated by the sign "○", and there is a possibility that only the reflected wave signal is influenced by the other pieces of data. Thus, the determination unit 116 does not determine that the second ultrasound diagnosis apparatus is in a failed state, and determines that there is a possibility of a failure.

In case 5, the reflected wave signal, the signal processing data, and the ultrasound image data are all indicated by the sign "○". The determination unit 116 determines that the second ultrasound diagnosis apparatus is in the normal state.

In case 6, the reflected wave signal and the signal processing data are indicated by the sign "○", and the ultrasound image data is indicated by the sign "×". Although the determination of the reflected wave signal and the signal processing data and the determination of the ultrasound image data are different from each other, the determination in the upstream processing in the ultrasound diagnosis apparatus takes priority. Since the reflected wave signal and the signal processing data are indicated by the sign "○", the determination unit 116 determines that the second ultrasound diagnosis apparatus is in the normal state.

In case 7, the reflected wave signal and the ultrasound image data are indicated by the sign "○", and the signal processing data is indicated by the sign "×". Since the reflected wave signal is indicated by the sign "○", then the determination unit 116 determines that the second ultrasound diagnosis apparatus is in the normal state based on the above-described priority relationship.

In case 8, the reflected wave signal is indicated by the sign "○", and the ultrasound image data and the signal processing data are indicated by the sign "×". Although the reflected wave signal is indicated by the sign "○", the other two pieces of data are indicated by the sign "×", and there is a possibility that only the reflected wave signal is influenced by the other pieces of data. Thus, the determination unit 116 does not determine that the second ultrasound diagnosis apparatus is in the normal state, and determines that there is a possibility of a failure.

Cases 9 to 12 are forms in which the state of the second ultrasound diagnosis apparatus is determined using two pieces of data (the signal processing data and the ultrasound image data).

In cases 9 and 10, the signal processing data is indicated by the sign "×". The determination in the upstream processing in the ultrasound diagnosis apparatus takes priority, and the priority relationship is as follows: the determination of the signal processing data >the determination of the ultrasound image data. Since the signal processing data is indicated by the sign "×", the determination unit 116 determines that the second ultrasound diagnosis apparatus is in a failed state.

In cases 11 and 12, the signal processing data is indicated by the sign "○". The determination in the upstream processing in the ultrasound diagnosis apparatus takes priority, and the priority relationship is as follows: the determination of the signal processing data >the determination of the ultrasound image data. Since the signal processing data is indicated by the sign "○", the determination unit 116 determines that the second ultrasound diagnosis apparatus is in the normal state.

Figure 8:
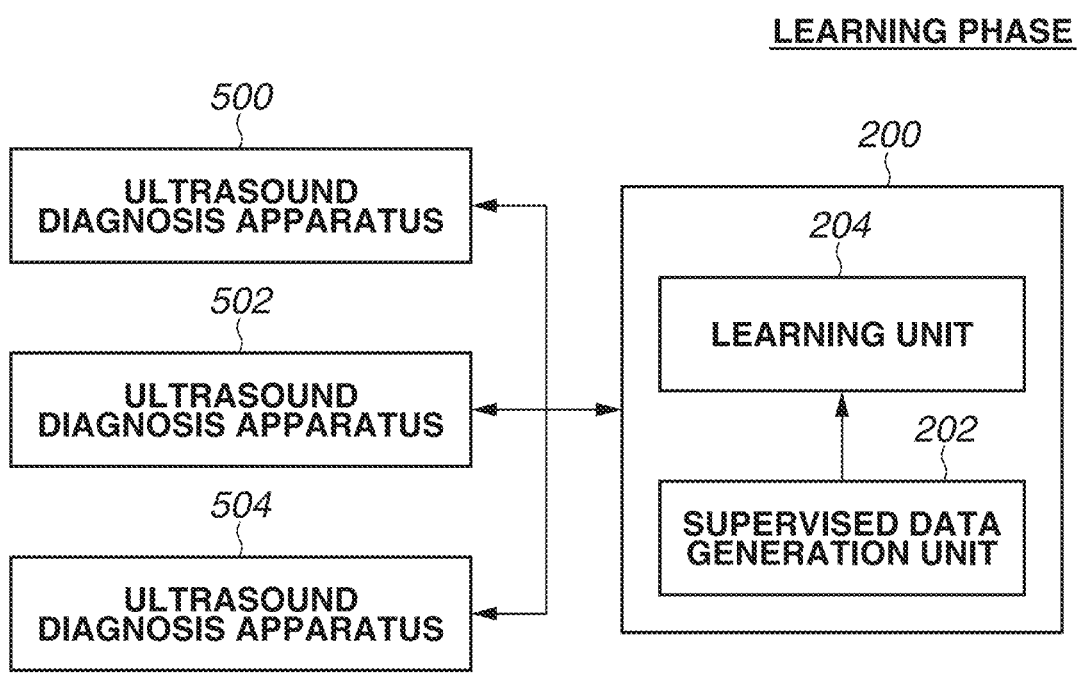
FIG. 8 is a diagram illustrating an example where a learning device according to the first exemplary embodiment of the present invention is installed outside the ultrasound diagnosis apparatus.

The learning device 200 may be installed outside the ultrasound diagnosis apparatus. FIG. 8 illustrates an example where the learning device 200 is installed outside the ultrasound diagnosis apparatus.

The learning device 200 may be located, for example, on a network in a hospital or on a cloud outside the hospital. The learning device 200 is connected to a plurality of ultrasound diagnosis apparatuses 500, 502, and 504. Although an example is illustrated in which three ultrasound diagnosis apparatuses are connected to the learning device 200, four or more ultrasound diagnosis apparatuses may be connected to the learning device 200.

For example, the learning device 200 learns data on a failed state generated in the ultrasound diagnosis apparatus 500 as supervised data, thereby generating a trained model. The learning device 200 also learns data on a failed state generated in the ultrasound diagnosis apparatus 502 different from the ultrasound diagnosis apparatus 500 as supervised data, thereby updating the trained model. Similarly, the learning device 200 learns data on a failed state generated in the ultrasound diagnosis apparatus 504 different from the ultrasound diagnosis apparatus 500 and the ultrasound diagnosis apparatus 502 as supervised data, thereby updating the trained model. The trained model generated (updated) in the learning device 200 is transmitted to each of the plurality of ultrasound diagnosis apparatuses 500, 502, and 504. Each of the plurality of ultrasound diagnosis apparatuses 500, 502, and 504 stores the latest trained model generated by the learning device 200.

As described above, the learning device 200 can learn pieces of data on failed states set in the plurality of ultrasound diagnosis apparatuses 500, 502, and 504 as supervised data. Thus, the learning device 200 can generate a trained model corresponding to each of the plurality of ultrasound diagnosis apparatuses 500, 502, and 504. The learning device 200 can also collectively learn the pieces of data on the failed states generated in the plurality of ultrasound diagnosis apparatuses 500, 502, and 504 as supervised data. The plurality of ultrasound diagnosis apparatuses 500, 502, and 504 can serve as both the first and second ultrasound diagnosis apparatuses.

Figure 9:
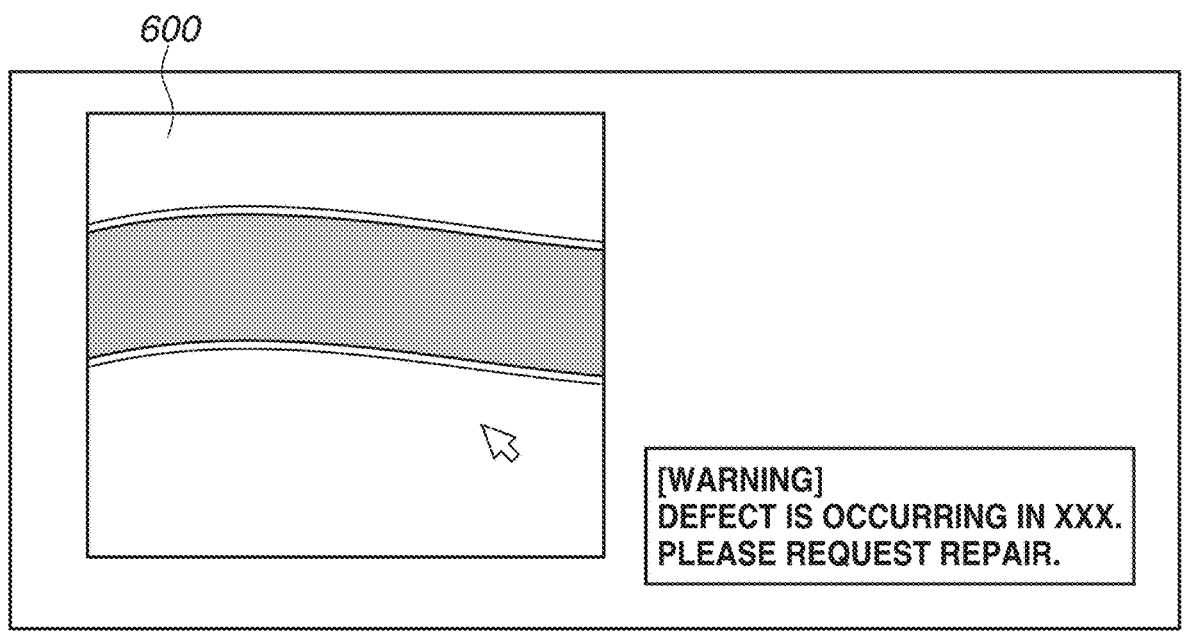
FIG. 9 is a diagram illustrating a display form of a display unit in the ultrasound diagnosis apparatus according to the first exemplary embodiment of the present invention.

Next, with reference to FIG. 9, the notification form (the display form) of the notification unit 108 (the display unit 106) is described. The notification unit 108 notifies the operator that the determination unit 116 determines that the second ultrasound diagnosis apparatus is in a failed state. In this case, the notification unit 108 may also notify the operator of a failure portion in addition to the notification that the second ultrasound diagnosis apparatus is in a failed state.

Using a trained model trained to determine a failure using data generated in the second ultrasound diagnosis apparatus, the inference unit 208 checks ultrasound image data 600 displayed on the display unit 106 and data in the ultrasound diagnosis apparatus and determines the presence or absence of a failure.

Then, if the inference unit 208 determines that the second ultrasound diagnosis apparatus is in a failed state, the notification unit 108 notifies the operator of the determination result. The notification unit 108 may function as the display function of the display unit 106, or may notify the operator using an alarm sound. In a case where the second ultrasound diagnosis apparatus determines that the second ultrasound diagnosis apparatus is in a failed state, the second ultrasound diagnosis apparatus not only notifies the operator of the determination result by displaying the notification on the display unit 106 but also additionally displays contact information regarding a request for repair on the display unit 106. The notification unit 108 may notify a call center. Regarding the notification of the notification unit 108, any approach may be taken to prevent the ultrasound diagnosis from being affected, and it is not limited to a particular approach.

Figure 10:
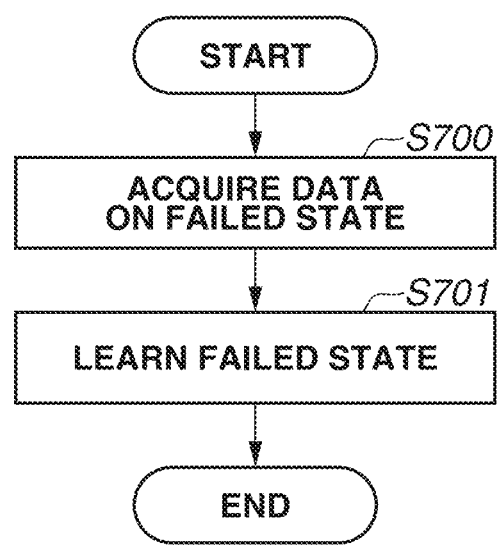
FIG. 10 is a diagram illustrating an operation regarding the learning phase according to the first exemplary embodiment of the present invention.

With reference to FIG. 10, the operation regarding the learning phase in the ultrasound diagnosis apparatus is described below.

In step S700, data on a failed state is acquired in the first ultrasound diagnosis apparatus. For example, as data generated in the first ultrasound diagnosis apparatus, a reflected wave signal, signal processing data, and ultrasound image data that are obtained in an actually failed state or a simulated failed state can be the data on the failed state. Alternatively, simulated data on a failed state generated by an external apparatus of the first ultrasound diagnosis apparatus may be input to the first ultrasound diagnosis apparatus.

In step S701, the learning device 200 learns the data on the failed state as supervised data, thereby generating a trained model. After step S701, the operation regarding the learning phase ends.

Next, with reference to FIG. 11, the operation regarding the inference phase in the ultrasound diagnosis apparatus is described.

FIG. 11 illustrates a case where a failure determination is made using, as target data, data before ultrasound image data is generated from the data in the second ultrasound diagnosis apparatus.

In step S800, the transmission/reception unit 110 causes the ultrasound probe 100 to transmit and receive an ultrasound wave. The ultrasound probe 100 may transmit and receive the ultrasound wave in the air.

In step S801, the determination unit 116 makes a failure determination using at least one of reflected wave signal data, signal processing data, and ultrasound image data acquired based on the ultrasound wave transmitted and received by the ultrasound probe 100.

If a failure is detected (YES in step S801), the processing proceeds to step S803. In step S803, the notification unit 108 gives the operator a warning. Then, in step S802, the ultrasound image generation unit 114 generates an ultrasound image.

If a failure is not detected (NO in step S801), the processing immediately proceeds to step S802. In step S802, the ultrasound image generation unit 114 generates an ultrasound image.

In step S802, the ultrasound image generation unit 114 generates an ultrasound image using the data generated in step S801. In this step, the ultrasound image generation unit 114 can also perform image processing for improving the visibility of the ultrasound image.

In step S806, in addition to the ultrasound image generated by the ultrasound image generation unit 114, the notification unit 108 (the display unit 106) displays a warning if a failure is detected. After step S806, the operation regarding the inference phase ends.

Next, with reference to FIG. 12, the operation regarding the inference phase in the ultrasound diagnosis apparatus is described.

FIG. 12 illustrates a case where a failure determination is made using, as target data, ultrasound image data generated in the second ultrasound diagnosis apparatus.

In step S800, the transmission/reception unit 110 causes the ultrasound probe 100 to transmit and receive an ultrasound wave. The ultrasound probe 100 may transmit and receive the ultrasound wave in the air.

In step S802, using signal processing data obtained by the signal processing unit 112 performing various types of signal processing on a reflected wave signal received by the transmission/reception unit 110, the ultrasound image generation unit 114 generates ultrasound image data. In this step, in addition to the signal processing, the ultrasound image generation unit 114 can also perform image processing for improving the visibility of the ultrasound image.

In step S804, the determination unit 116 makes a failure determination using the ultrasound image data generated by the ultrasound image generation unit 114 in step S802. If a failure is detected (YES in step S804), the processing proceeds to step S805. In step S805, the notification unit 108 (the display unit 106) displays a warning. Then, in step S806, the display unit 106 displays the ultrasound image.

If a failure is not detected (NO in step S804), the processing immediately proceeds to step S806. In step S806, the display unit 106 displays the ultrasound image.

In step S806, in addition to the ultrasound image generated by the ultrasound image generation unit 114, the display unit 106 displays a warning if a failure is detected. After step S806, the operation regarding the inference phase ends.

As described above, a failure determination apparatus of an ultrasound diagnosis apparatus according to the present exemplary embodiment includes the determination unit 116 that determines whether the second ultrasound diagnosis apparatus is in a failed state based on data generated in the second ultrasound diagnosis apparatus using a trained model trained on data generated in the first ultrasound diagnosis apparatus in a failed state as supervised data, and the notification unit 108 that notifies the operator of the determination result of the determination unit 116. Thus, according to the present exemplary embodiment, it is possible to make a failure determination in the ultrasound diagnosis apparatus with high accuracy.

Alternatively, a trained model may be generated using the ultrasound diagnosis apparatus in a normal state. The determination unit 116 may determine whether the second ultrasound diagnosis apparatus is in a failed state based on data generated in the second ultrasound diagnosis apparatus using a trained model trained on data generated in a third ultrasound diagnosis apparatus in a normal state as supervised data. The ultrasound diagnosis apparatus failure determination apparatus includes a learning device that learns a reflected wave signal received by the transmission/reception unit 110, signal processing data subjected to signal processing by the signal processing unit 112, and ultrasound image data generated by the ultrasound image generation unit 114 in the third ultrasound diagnosis apparatus in the normal state, thereby generating a trained model. The determination unit 116 determines whether the second ultrasound diagnosis apparatus is in a failed state based on data generated in the second ultrasound diagnosis apparatus using the trained model. Then, the notification unit 108 notifies the operator of the determination result of the determination unit 116.

With reference to FIGS. 13 and 14, an ultrasound diagnosis apparatus according to a second exemplary embodiment of the present invention is described. The second exemplary embodiment is different from the first exemplary embodiment in that, in a case where the second ultrasound diagnosis apparatus is in a failed state, the control unit 118 performs the process of correcting data on the failed state of the second ultrasound diagnosis apparatus in the second exemplary embodiment. For example, the control unit 118 corrects the data on the failed state of the second ultrasound diagnosis apparatus using data obtained when the second ultrasound diagnosis apparatus is a normal state, i.e., when it is determined that the second ultrasound diagnosis apparatus is not in a failed state.

Although not illustrated, in the second exemplary embodiment of the present invention, the learning device 200 learns data on a normal state and data on a failed state of the first ultrasound diagnosis apparatus in association with each other in the learning phase.

With reference to FIG. 13, the operation regarding the inference phase in the second ultrasound diagnosis apparatus is described. FIG. 13 illustrates a case where a failure determination is made using, as target data, data before ultrasound image data is generated from the data in the second ultrasound diagnosis apparatus.

In step S800, the transmission/reception unit 110 causes the ultrasound probe 100 to transmit and receive an ultrasound wave. The ultrasound probe 100 may transmit and receive the ultrasound wave in the air.

In step S801, the ultrasound diagnosis apparatus makes a failure determination using a reflected wave signal and signal processing data acquired based on the ultrasound wave transmitted and received by the ultrasound probe 100.

If a failure is detected (YES in step S801), the processing proceeds to step S803. In step S803, the notification unit 108 (the display unit 106) displays a warning. At the same time, in the process of step S813, the control unit 118 corrects the data on the failed state. In step S802, the ultrasound image generation unit 114 generates an ultrasound image. This processing can simply recover the ultrasound diagnosis apparatus from the failed state.

If a failure is not detected (NO in step S801), the processing immediately proceeds to step S802. In step S802, the ultrasound image generation unit 114 generates an ultrasound image.

In step S802, the ultrasound image generation unit 114 generates an ultrasound image using the data generated in step S801. In this step, the ultrasound image generation unit 114 also performs image processing for improving the visibility of the ultrasound image.

In step S806, the display unit 106 displays the ultrasound image generated by the ultrasound image generation unit 114. If a failure is detected, the notification unit 108 displays a warning. After step S806, the operation regarding the inference phase ends.

FIG. 14 illustrates a case where a failure determination is made using ultrasound image data generated in the ultrasound diagnosis apparatus as target data.

In step S800, the transmission/reception unit 110 causes the ultrasound probe 100 to transmit and receive an ultrasound wave. The ultrasound probe 100 may transmit and receive the ultrasound wave in the air.

In step S802, the ultrasound image generation unit 114 generates ultrasound image data using signal processing data obtained by the signal processing unit 112 performing various types of signal processing on a reflected wave signal received by the transmission/reception unit 110. In this step, in addition to the signal processing, the ultrasound image generation unit 114 also performs image processing for improving the visibility of the ultrasound image.

In step S804, the ultrasound diagnosis apparatus makes a failure determination using the ultrasound image data generated by the ultrasound image generation unit 114. If a failure is detected (YES in step S804), the processing proceeds to step S805. In step S805, the notification unit 108 displays a warning on the display unit 106. At the same time, in step S815, the control unit 118 corrects the data on the failed state. In step S806, the display unit 106 displays the ultrasound image. This processing can simply recover the ultrasound diagnosis apparatus from the failed state.

If a failure is not detected (NO in step S804), the processing immediately proceeds to step S806. In step S806, the display unit 106 displays the ultrasound image.

In step S806, the display unit 106 displays the ultrasound image generated by the ultrasound image generation unit 114. If a failure is detected, the notification unit 108 also displays a warning. After step S806, the operation regarding the inference phase ends.

As described above, a failure determination apparatus of an ultrasound diagnosis apparatus according to the present exemplary embodiment can correct data generated in the second ultrasound diagnosis apparatus if it is determined that the second ultrasound diagnosis apparatus is in a failed state and simply recover the ultrasound diagnosis apparatus from the failed state.

A computer program for achieving the functions of the first and second exemplary embodiments can be supplied to a computer via a network or a storage medium (not illustrated) and executed. The computer program is a computer program for causing a computer to execute the above ultrasound image display method. That is, the computer program is a program for achieving the function of the ultrasound diagnosis apparatus using a computer. The storage medium stores the computer program.

In the first and second exemplary embodiments, if the types of ultrasound probes 100 connected to the ultrasound diagnosis apparatus are different from each other, a learning process and an inference process may be individually performed in an optimal manner for each of the types of ultrasound probes 100.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2020-095387, filed Jun. 1, 2020, which is hereby incorporated by reference herein in its entirety.

What is claimed is:

1. A failure determination apparatus of a second ultrasound diagnosis apparatus comprising:
   at least one memory storing one or more programs including instructions; and
   one or more processors which, by executing the instructions, function as:
      a determination unit configured to, using a plurality of trained models, determine whether the second ultrasound diagnosis apparatus is in a failed state based on states of multiple types of data generated in the second ultrasound diagnosis apparatus, the plurality of trained models including a first trained model generated by being trained using a reflected wave signal received by a first ultrasound diagnosis apparatus that is in the failed state, a second trained model generated by being trained using signal processing data obtained by performing signal processing on a reflected wave signal received by the first ultrasound diagnosis apparatus in the failed state, and a third trained model generated by being trained using ultrasound image data generated by the first ultrasound diagnosis apparatus in the failed state; and a notification unit configured to notify an operator of a result of the determination by the determination unit, wherein the determination unit determines whether or not the second ultrasound diagnosis apparatus is in the failed state by integrating respective states of the multiple types of data output using the plurality of trained models based on a priority configured to be set according to the multiple types of data, and wherein the priority is configured to be set to prioritize a reflected wave signal received by the second ultrasound diagnosis apparatus, signal processing data obtained by performing signal processing on the reflected wave signal received by the second ultrasound diagnosis apparatus and ultrasound image data generated by the second ultrasound diagnosis apparatus in this order, among the multiple types of data.

2. The failure determination apparatus of the ultrasound diagnosis apparatus according to claim 1, wherein the one or more processors, by executing the instructions, further function as a learning device configured to learn the multiple types of data generated in the first ultrasound diagnosis apparatus as supervised data and generate the plurality of trained models.

3. The failure determination apparatus of the ultrasound diagnosis apparatus according to claim 2, wherein the learning device generates the plurality of trained models by learning the multiple types of data generated in the first ultrasound diagnosis apparatus as supervised data in an associated manner using a neural network.

4. The failure determination apparatus of the ultrasound diagnosis apparatus according to claim 2, further comprising a storage configured to store the plurality of trained models generated by the learning device.

5. The failure determination apparatus of the ultrasound diagnosis apparatus according to claim 2, wherein the learning device is installed outside the first ultrasound diagnosis apparatus.

6. The failure determination apparatus of the ultrasound diagnosis apparatus according to claim 5, wherein the learning device learns the multiple types of data generated in a plurality of first ultrasound diagnosis apparatuses in the failed state as supervised data.

7. The failure determination apparatus of the ultrasound diagnosis apparatus according to claim 2, wherein the learning device generates the plurality of trained models corresponding to respective types of the multiple types of data generated in the first ultrasound diagnosis apparatus.

8. The failure determination apparatus of the ultrasound diagnosis apparatus according to claim 1, wherein a degree of priority is set according to a type of data of the multiple types of data generated in the second ultrasound diagnosis apparatus, and the determination unit determines whether the second ultrasound diagnosis apparatus is in the failed state according to the degree of priority.

9. The failure determination apparatus of the ultrasound diagnosis apparatus according to claim 8, wherein the degree of priority is set by the operator.

10. The failure determination apparatus of the ultrasound diagnosis apparatus according to claim 9, wherein a weight is set for the degree of priority according to processing content with respect to the type of the data.

11. The failure determination apparatus of the ultrasound diagnosis apparatus according to claim 8, wherein weights are set for respective degrees of priority of a reflected wave signal, signal processing data, and ultrasound image data in this order.

12. The failure determination apparatus of the ultrasound diagnosis apparatus according to claim 1, wherein the one or more processors, by executing the instructions, further function as a control unit configured to, in a case where the second ultrasound diagnosis apparatus is in the failed state, perform a process of correcting the types of data on the failed state of the second ultrasound diagnosis apparatus.

13. A failure determination method comprising:
determining, using a plurality of trained models, whether a second ultrasound diagnosis apparatus is in a failed state based on states of multiple types of data generated in the second ultrasound diagnosis apparatus, the plurality of trained models including a first trained model generated by being trained using a reflected wave signal received by a first ultrasound diagnosis apparatus that is in the failed state, a second trained model generated by being trained using signal processing data obtained by performing signal processing on a reflected wave signal received by the first ultrasound diagnosis apparatus in the failed state, and a third trained model generated by being trained using ultrasound image data generated by the first ultrasound diagnosis apparatus in the failed state; and notifying an operator of a result of the determination in the determining, wherein the determining determines whether or not the second ultrasound diagnosis apparatus is in the failed state by integrating respective states of the multiple types of data output using the plurality of trained models based on a priority configured to be set according to the multiple types of data, and wherein the priority is configured to be set such that to prioritize a reflected wave signal received by the second ultrasound diagnosis apparatus, signal processing data obtained by performing signal processing on the reflected wave signal received by the second ultrasound diagnosis apparatus and ultrasound image data generated by the second ultrasound diagnosis apparatus in this order, among the multiple types of data.

14. A non-transitory computer-readable storage medium storing one or more programs including instructions for causing a computer to execute a failure determination method, the failure determination method comprising:
determining, using a plurality of trained models, whether a second ultrasound diagnosis apparatus is in a failed state based on states of multiple types of data generated in the second ultrasound diagnosis apparatus, the plurality of trained models including a first trained model generated by being trained using a reflected wave signal received by a first ultrasound diagnosis apparatus that is in the failed state, a second trained model generated by being trained using signal processing data obtained by performing signal processing on a reflected wave signal received by the first ultrasound diagnosis apparatus in the failed state, and a third trained model generated by being trained using ultrasound image data generated by the first ultrasound diagnosis apparatus in the failed state; and notifying an operator of a result of the determination in the determining, wherein the determining determines whether or not the second ultrasound diagnosis apparatus is in the failed state by integrating respective states of the multiple types of data output using the plurality of trained models based on a priority configured to be set according to the multiple types of data, and wherein the priority is configured to be set to prioritize a reflected wave signal received by the second ultrasound diagnosis apparatus, signal processing data obtained by performing signal processing on the reflected wave signal received by the second ultrasound diagnosis apparatus and ultrasound image data generated by the second ultrasound diagnosis apparatus in this order, among the multiple types of data.

\* \* \* \* \*